(12) United States Patent
Shiono et al.

(10) Patent No.: US 7,998,150 B2
(45) Date of Patent: Aug. 16, 2011

(54) SUTURING DEVICE

(75) Inventors: Junji Shiono, Yokohama (JP); Yuta Muyari, Tokyo (JP); Kensuke Hayashi, Yokohama (JP)

(73) Assignee: Olympus Medical Systems Corp., Tokyo (JP)

( * ) Notice: Subject to any disclaimer, the term of this patent is extended or adjusted under 35 U.S.C. 154(b) by 879 days.

(21) Appl. No.: 11/863,899

(22) Filed: Sep. 28, 2007

(65) Prior Publication Data

US 2009/0088780 A1    Apr. 2, 2009

(51) Int. Cl.
*A61B 17/10*    (2006.01)
(52) U.S. Cl. .......................... 606/144; 606/139; 606/232
(58) Field of Classification Search .......... 606/139–145, 606/151, 158, 232, 213, 215
See application file for complete search history.

(56) References Cited

U.S. PATENT DOCUMENTS

| 4,235,238 | A * | 11/1980 | Ogiu et al. | 606/145 |
| 2004/0249392 | A1 * | 12/2004 | Mikkaichi et al. | 606/142 |
| 2007/0027476 | A1 | 2/2007 | Harris et al. | |
| 2007/0112362 | A1 | 5/2007 | Mikkaichi et al. | |

FOREIGN PATENT DOCUMENTS

| EP | 1 938 760 A1 | 7/2008 |
| WO | WO 01/39671 A1 | 6/2001 |
| WO | WO 2004/071307 A2 | 8/2004 |
| WO | WO 2007/037326 A1 | 4/2007 |

* cited by examiner

*Primary Examiner* — Anhtuan Nguyen
*Assistant Examiner* — Tuan V Nguyen
(74) *Attorney, Agent, or Firm* — Scully, Scott, Murphy & Presser, P.C.

(57) ABSTRACT

A suturing device is disclosed which sutures a tissue using a suture unit having a suture thread with both ends fitted to a first anchor and a second anchor, respectively. The suturing device includes a hollow tip member receiving the first and second anchors; a wire having a front end inserted through the hollow tip member so that the first and second anchors can be released out from the hollow tip member; a flexible tube, a parallel member, a relative position holding member, a forward movement restricting member, and an operating portion. At least one of the hollow tip member, the forward movement restricting member, and the flexible tube has a communication portion on an outer peripheral surface thereof so as to communicate with an internal cavity, and a middle portion of the suture unit is inserted into the communication portion and is tied to the wire.

5 Claims, 16 Drawing Sheets

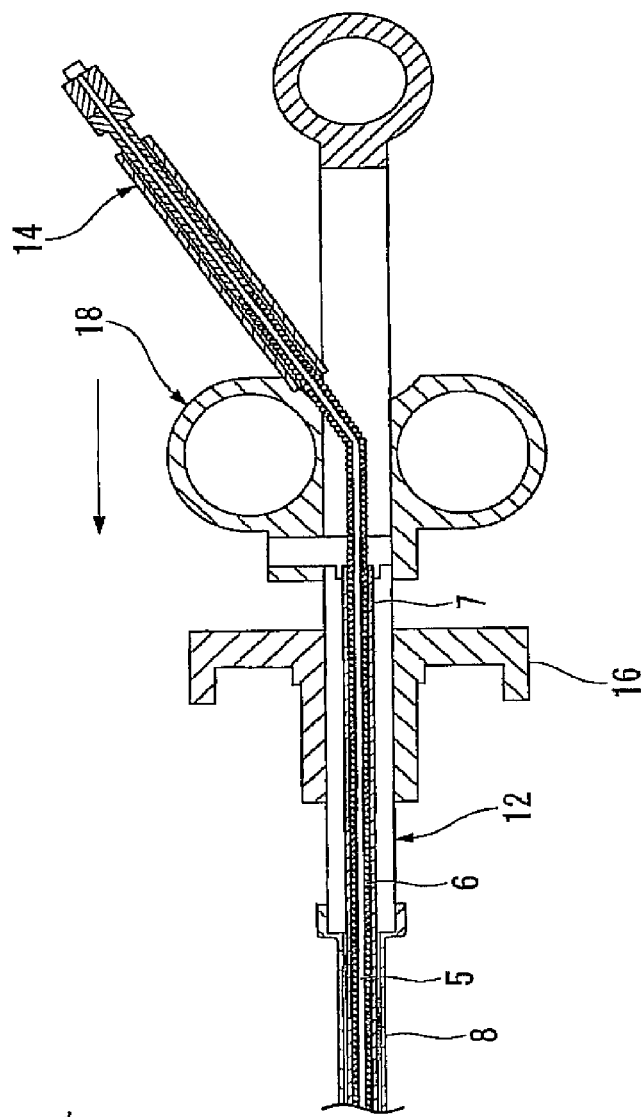
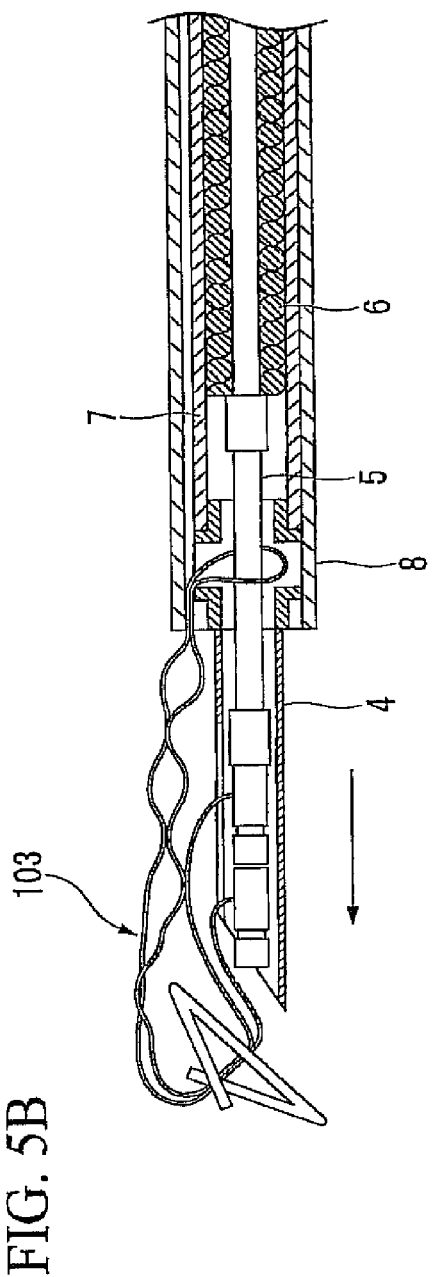
FIG. 5A
FIG. 5B

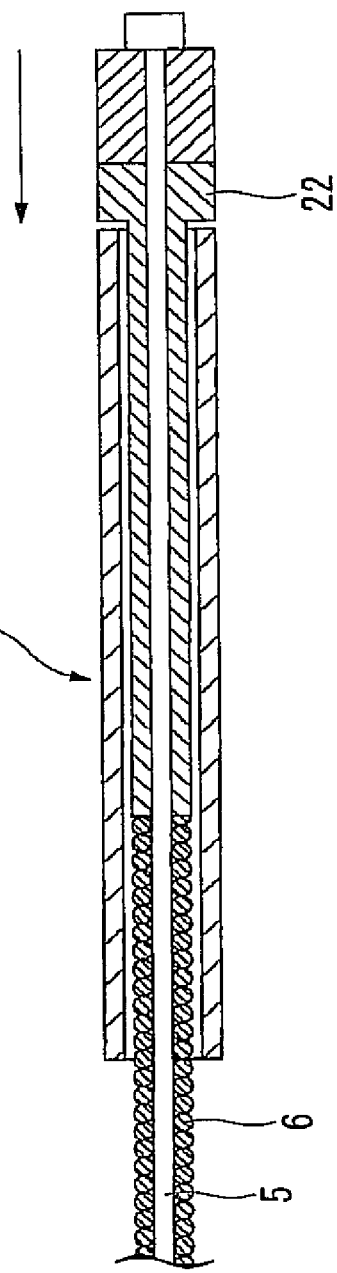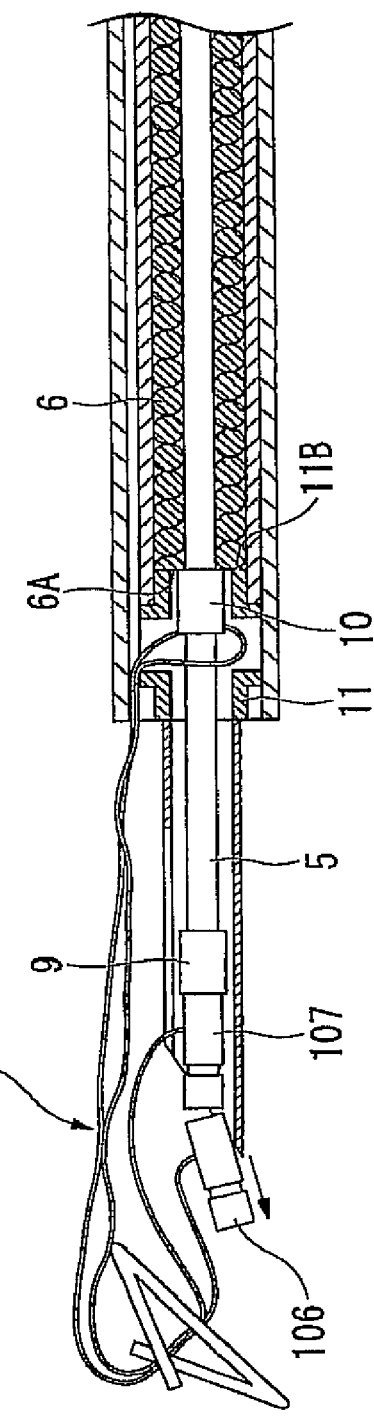
FIG. 7A
FIG. 7B

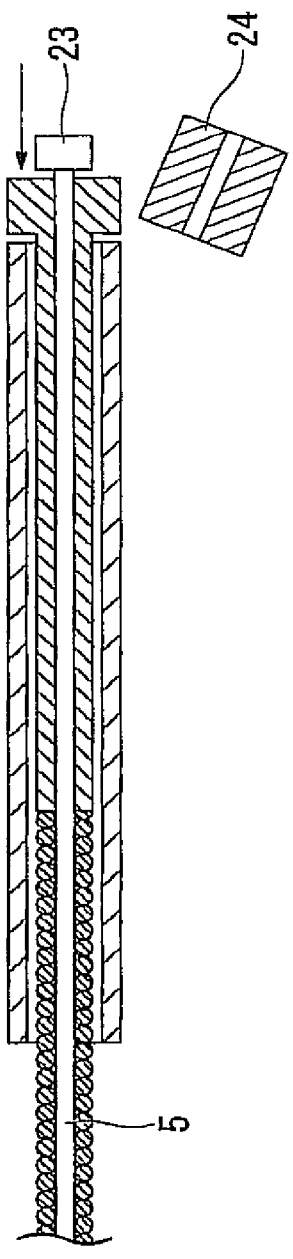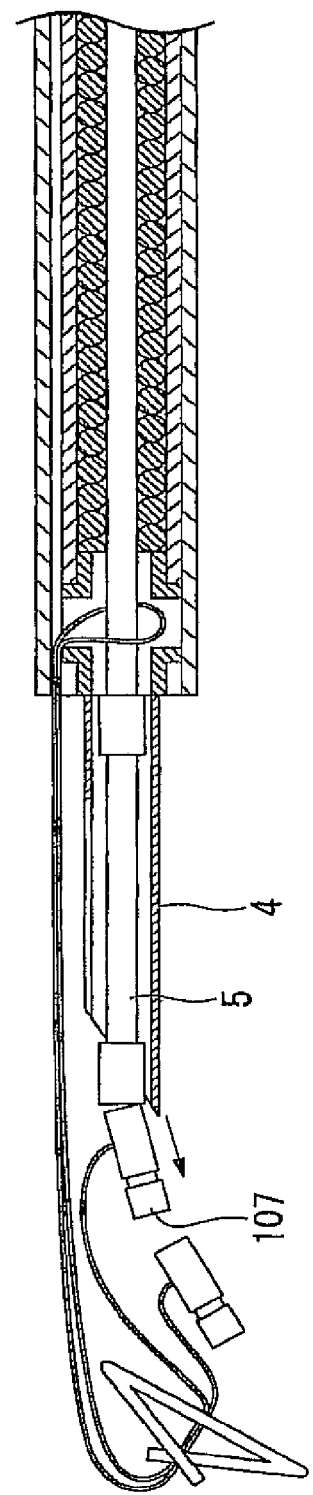
FIG. 9A
FIG. 9B

SUTURING DEVICE

BACKGROUND OF THE INVENTION

1. Field of the Invention

The present invention relates to a suturing device that is used by being inserted into a body cavity, and more particularly, to a suturing device that is used when suturing a perforation or the like formed in a lumen such as the stomach or the intestine with a suture thread having both ends fixed to an anchor.

2. Description of Related Art

In the past, for the purpose of suture of perforations, lacerations or the like formed in a lumen such as the stomach or the intestine, there has been known a suturing device that uses a suture thread having both ends fixed to an anchor (see WO 2007-37326, for example). In the suturing device, the anchors on both ends of the suture thread are placed to be locked at the tissues around the perforation at the inside or outside of the tissues, and the suture thread is pulled so that the tissues locked at the anchors are tightened up, thereby suturing the tissues.

In the suturing device disclosed in WO 2007-37326, in order to perform the suturing operation in a secure manner, it is necessary to release the anchors fitted to the distal end of the suturing device from the distal end so that only one anchor is released at a time so as to be locked at the opposite tissues around the perforation. For this reason, in the suturing device disclosed in WO 2007-37326, an annular groove is formed on the surface of the anchor so as to be engaged with a protrusion formed on the inner surface of a needle provided on the distal end of the suturing device. When the anchor is released, the groove disengages with the protrusion, which is transferred as a sense of feeling to a user so that the user can perceive the release of the anchor.

However, in the suturing device disclosed in WO 2007-37326, the needle at the distal end and an operating portion that the user operates are connected to a flexible sheath, and the sheath is expanded by the force applied to the released anchor. For this reason, the above-described sense of disengagement generated when the anchor is released is absorbed and attenuated by expansion and shrinkage of the sheath and is not sufficiently transferred to the user.

When the anchor is configured to engage with the needle more tightly in order to sufficiently transfer the sense of disengagement to the user even when the sheath absorbs the disengagement impact, a greater force may be required to release the engagement. As a result, there may be a case in which two anchors are released at a time, making it difficult to perform the suturing operation properly.

SUMMARY OF THE INVENTION

The present invention was contrived to solve the above-mentioned problems. An object of the present invention is to provide an endoscopic treatment tool capable of releasing an anchor from a distal end thereof in a secured manner and only one by one at a time.

According to a first aspect of the present invention, there is provided a suturing device that sutures a tissue using a suture unit having a suture thread with both ends fitted to a first anchor and a second anchor, respectively, the suturing device including: a hollow tip member receiving the first and second anchors; a wire having a front end inserted through the hollow tip member so that the first and second anchors can be released out from the hollow tip member; a flexible tube having a distal end integrally connected at a proximal end of the hollow tip member, through which the wire is inserted so as to freely move forward and backward in the axial direction of the tube; a parallel member inserted through the flexible tube so as to freely move forward and backward in the axial direction of the tube along with the wire; a relative position holding member fitted to the wire so as to hold a relative positional relationship between the wire and the parallel member so as to remain construct; a forward movement restricting member provided on the flexible tube or the hollow tip member so as to restrict a forward movement of the parallel member; and an operating portion provided at a proximal end side of the wire and the parallel member so as to operate the wire and the parallel member, wherein in a state in which the relative positional relationship between the wire and the parallel member is held constant by the relative position holding member, when the wire is moved in the forward direction until the forward movement of the parallel member is restricted by the forward movement restricting member, only the first anchor is released out from the tip member by the movement of the wire, and wherein at least one of the hollow tip member, the forward movement restricting member, and the flexible tube has a communication portion on an outer peripheral surface thereof so as to communicate with an internal cavity, and a middle portion of the suture unit is inserted into the communication portion and is tied to the wire.

According to a second aspect of the present invention, there is provided a suturing device that sutures a tissue using a suture unit having a suture thread with both ends fitted to a first anchor and a second anchor, respectively, the suturing device including: a hollow tip member receiving the first and second anchors; a wire having a front end inserted through the tip member so that the first and second anchors can be released out from the tip member; a flexible tube having a distal end integrally connected at a proximal end of the tip member, through which the wire is inserted so as to freely move forward and backward in the axial direction of the tube; a first stopper provided on the wire so as to protrude away from the radial direction of the wire; a forward movement restricting member formed of an elastic material and provided on the tube or the tip member so as to restrict a forward movement of the first stopper; and an operating portion provided at a proximal end side of the wire and the first stopper so as to operate the wire and the first stopper, wherein when the wire is moved in the forward direction until the forward movement of the first stopper is restricted by the forward movement restricting member, the first anchor is released out from the tip member by the movement of the wire, and when the wire receives a force greater than a predetermined value, the forward movement restricting member is elastically deformed to enable the first stopper to move past the forward movement restricting member.

BRIEF DESCRIPTION OF THE DRAWINGS

FIG. 5A is an enlarged sectional view of the operating portion of the suturing device in the operating state, and FIG. 5B is an enlarged sectional view of the distal end portion of the suturing device in the operating state.

FIG. 7A is an enlarged sectional view of a tip operating portion of the suturing device in the operating state, and FIG. 7B is an enlarged sectional view of the distal end portion of the suturing device in the operating state.

FIG. 9A is an enlarged sectional view of a tip operating portion of the suturing device in the operating state, and FIG. 9B is an enlarged sectional view of the distal end portion of the suturing device in the operating state.

DESCRIPTION OF THE PREFERRED EMBODIMENTS

Hereinafter, a suturing device in accordance with a first embodiment of the present invention will be described with reference to FIGS. 1 to 11.

Figure 1:
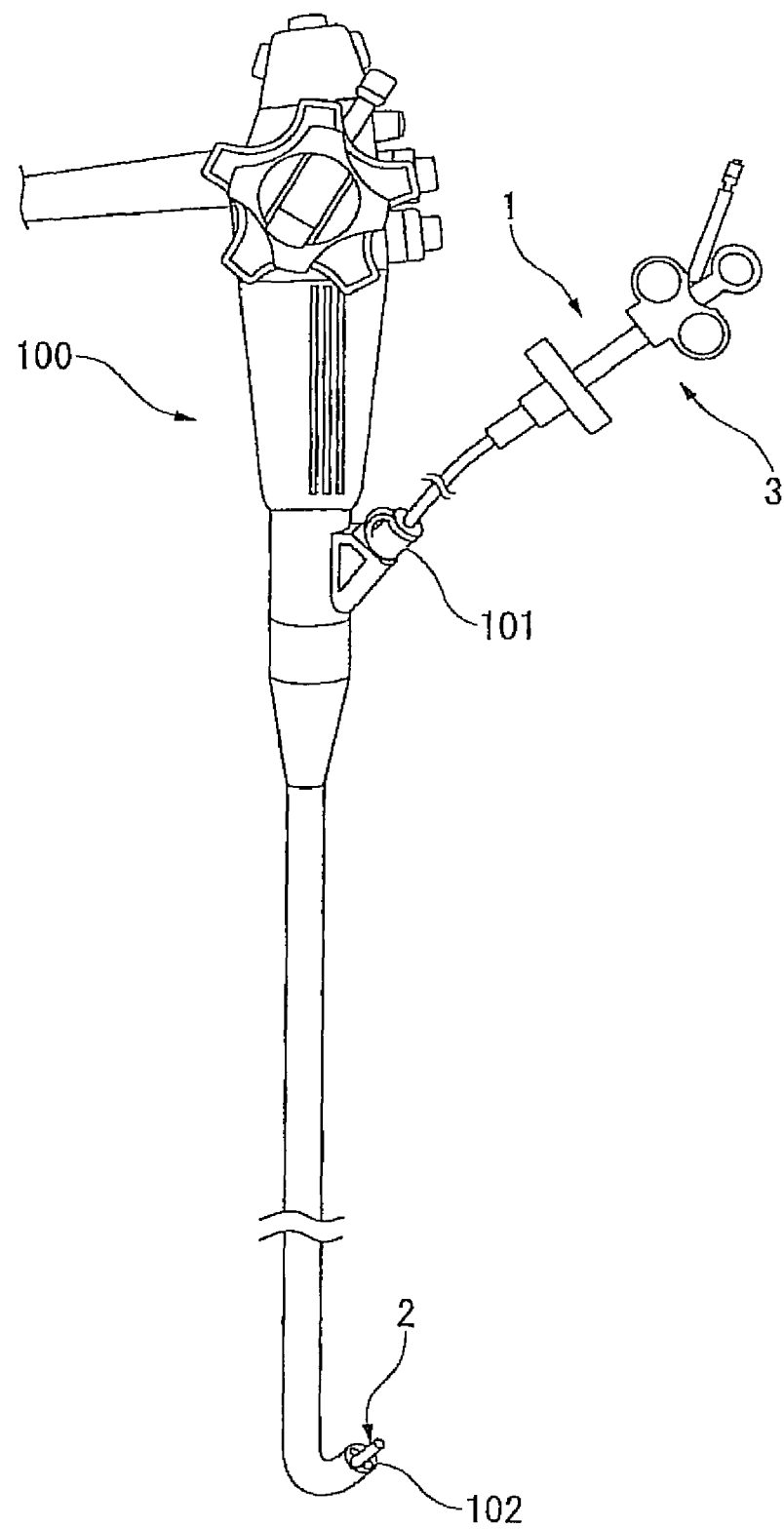
FIG. 1 is a diagram showing a suturing device in accordance with a first embodiment of the present invention.

FIG. 1 shows a suturing device 1 of the present embodiment. The suturing device 1 is used by being inserted into a forceps mouth 101 of an endoscope 100 and making a distal end thereof protrude out from an endoscope channel 102 inside the body of a patient or the like.

The suturing device 1 is configured to include a distal end portion 2 that is inserted into the body, and an operating portion 3 for operating various mechanisms installed in the distal end portion 2.

Figure 2:
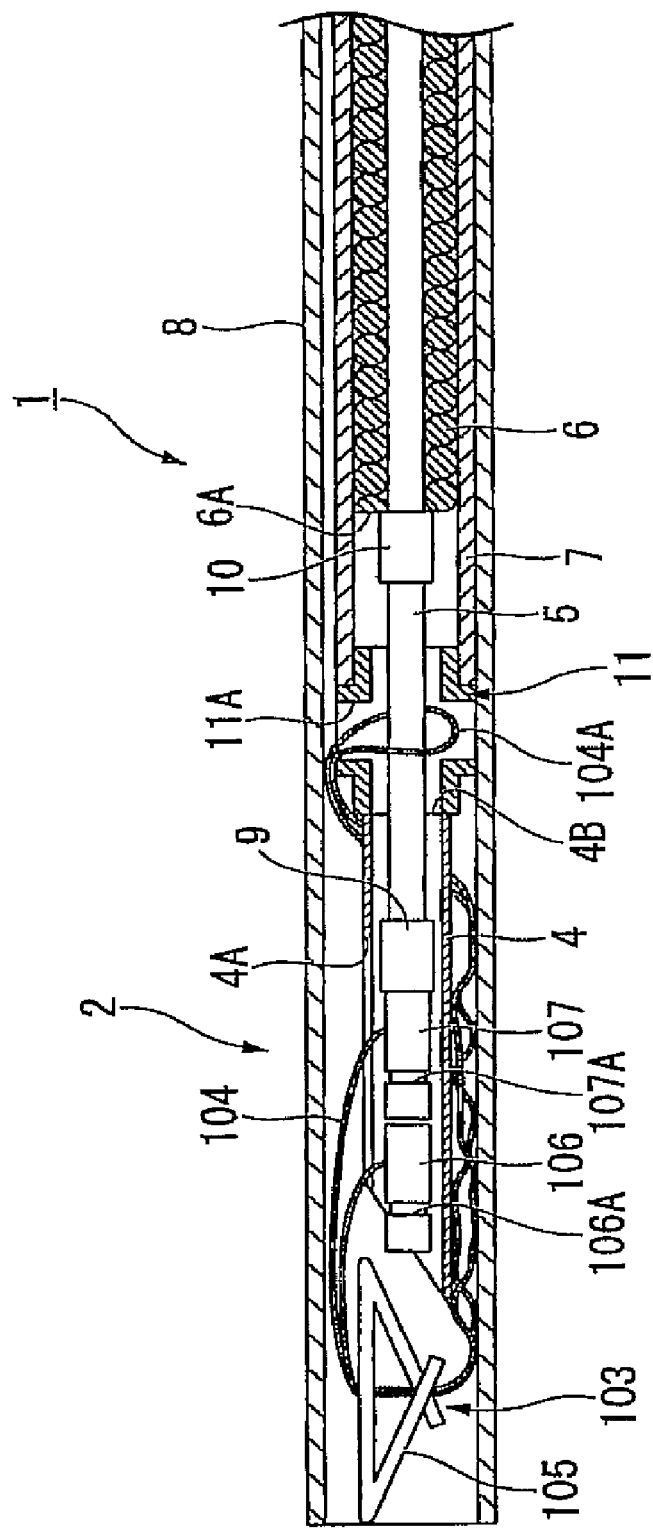
FIG. 2 is an enlarged sectional view of a distal end portion of the suturing device.

FIG. 2 is an enlarged sectional view of the distal end portion 2. The distal end portion 2 is configured to include a needle (a tip member) 4 that is fitted to a suture unit described later, a wire 5 that is inserted into the needle 4, a second sheath (a parallel member) 6, a tube 7 through which is inserted a second sheath 6 and the wire 5 so as to freely move forward and backward in the axial direction of the tube 7 and which is integrally fixed to the needle 4 at the proximal end side, and a first sheath (a sheath) 8 through which is inserted the tube 7.

The needle 4 is a hollow member made of metal or the like, and a groove 4A is formed on the top surface thereof. Anchors of the suture unit are received in the inside of the needle 4.

Figure 3:
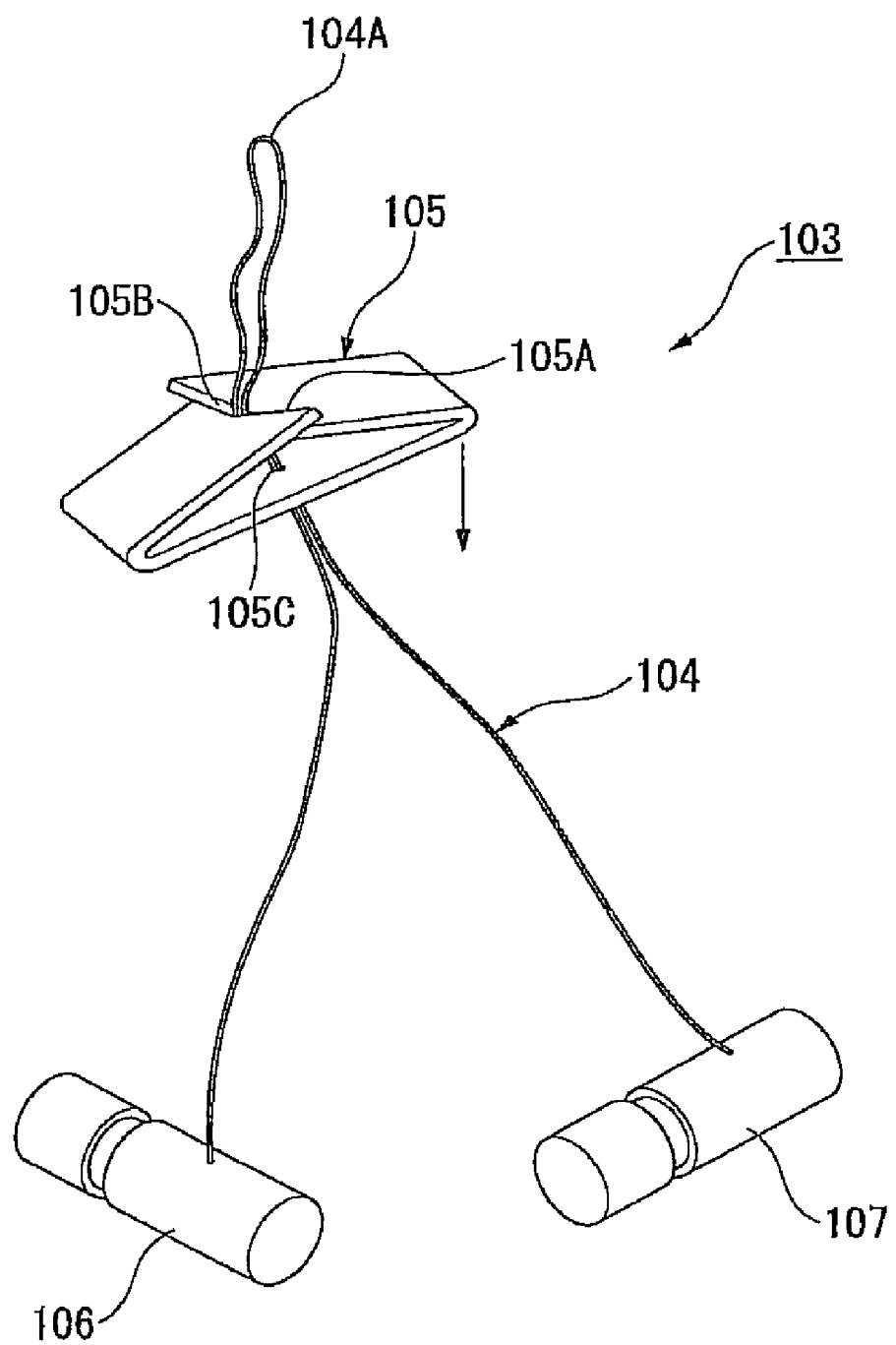
FIG. 3 is a diagram showing a suture unit that is used in the suturing device.

FIG. 3 is a diagram showing the suture unit 103 that is received in the needle 4. The suture unit 103 is configured to include a suture thread 104, a stopper 105 through which is inserted the suture thread 104, first and second rod-shaped anchors 106 and 107 that are fitted to both ends of the suture thread 104.

The stopper 105 is a plate-shaped member made of metal, a biodegradable resin, or the like. The stopper 105 is folded so that left and right end portions 105A and 105B are opposed to each other and are engaged with each other.

A hole 105C is formed at the substantially central portion in the longitudinal direction of the stopper 105. The suture thread 104 is folded at a mid-point portion 104A, and the suture thread 104 is inserted through the hole 105C from the opposite surface of the end portions 105A and 105B so as to pass between the end portions 105A and 105B that are engaged with each other. Operations of the stopper 105 in the operating state will be described later.

As shown in FIG. 2, the first and second anchors 106 and 107 of the suture unit 103 are received in the needle and are linearly aligned in the axial direction with the first anchor 106 disposed at the more distal end side. The suture thread 104 connected to the anchors 106 and 107 are exposed from a groove 4A to the outside of the needle 4.

Incidentally, engagement grooves 106A and 107A are formed on the entire circumference at a portion of the outer surface of each of the first and second anchors 106 and 107, respectively. Each of the engagement grooves 106A and 107A engages with an engagement protrusion (not shown) that is provided on the inner cavity of the needle 4, thereby preventing erroneous release of the anchors 106 and 107 or natural separation thereof when the distal end of the needle 4 is perpendicularly held to face downward.

The wire 5 is formed of metal or the like, and a distal end thereof is inserted through the needle 4 from the proximal end 4B of the needle 4. A pressing member 9 is mounted at the distal end of the wire 5. When the wire 5 is moved in the forward direction in the axial direction toward the distal end of the needle 4, the pressing member 9 is pressed against the first and second anchors 106 and 107, thereby allowing the anchors 106 and 107 to be released out from the needle 4.

The wire 5 is preferably a single wire that can transfer the pressing force applied from the operating portion 3 to the pressing member 9 in an appropriate manner. However, a multi-line wire obtained by twisting a number of metallic strands, a coil wire obtained by winding a number of metallic strands or a multi-line wire in a coil, or other wires may be used.

At a position separated at a predetermined distance from the pressing member 9 of the wire 5, an annular contact member (a relative position holding member) 10 is fixed to hold the relative positional relationship between the wire 5 and the second sheath 6 in a constant manner. The outer diameter of the contact member 10 is set such that the contact member 10 can freely move forward and backward within the inside of the needle 4. Incidentally, the shape of the contact member 10 is not limited to the annular shape as long as the contact member 10 is protruded away from the radial direction of the wire 5.

The second sheath 6 is a coil sheath formed by winding metal strands or multi-line wires in a tubular shape, and the proximal end of the wire 5 is inserted through the second sheath so as to freely move forward and backward in the axial direction of the second sheath 6. The inner diameter of the second sheath 6 is set smaller than the outer diameter of the contact member 10 of the wire 5, and the contact member 10 abuts to a distal end 6A of the second sheath 6 and cannot enter the second sheath 6. That is, when the contact member 10 is abutted to the distal end 6A of the second sheath 6, the positional relationship between the wire 5 and the second sheath 6 is held constant.

The tube 7 is a flexible, tubular member made of resin or the like. As a material for the tube 7, a material that has a small expansion ratio in the axial direction is preferred. The tube 7 is integrally connected to the proximal end 413 of the needle 4 via a connection tube (a forward movement restricting member) 11 that is mounted on the distal end of the tube 7.

A through-hole 11A is formed on the outer surface of the connection tube 11 so as to be penetrated through the inner cavity of the connection tube 11. A mid-point portion 104A of the suture thread 104 of the suture unit 103 is inserted through the through-hole 11A into the inner cavity of the connection tube 11 and is tied to the wire 5 inserted into the inner cavity.

The inner diameter in the axial direction of the connection tube 11 is set greater than the outer diameter of the contact member 10 of the wire 5 and the contact member 10 can freely move forward and backward in the axial direction within the inside of the connection tube 1. On the other hand, the inner diameter in the axial direction of the connection tube 11 is set smaller than the outer diameter of the second sheath 6, and the second sheath 6 cannot enter the connection tube 11.

The first sheath 8 is a coil sheath having the same structure as the second sheath 6, and the tube 7 and the needle 4 integrally connected to the tube 7 are inserted through the first sheath 8 so as to freely move forward and backward in the axial direction of the first sheath 8.

Figure 4:
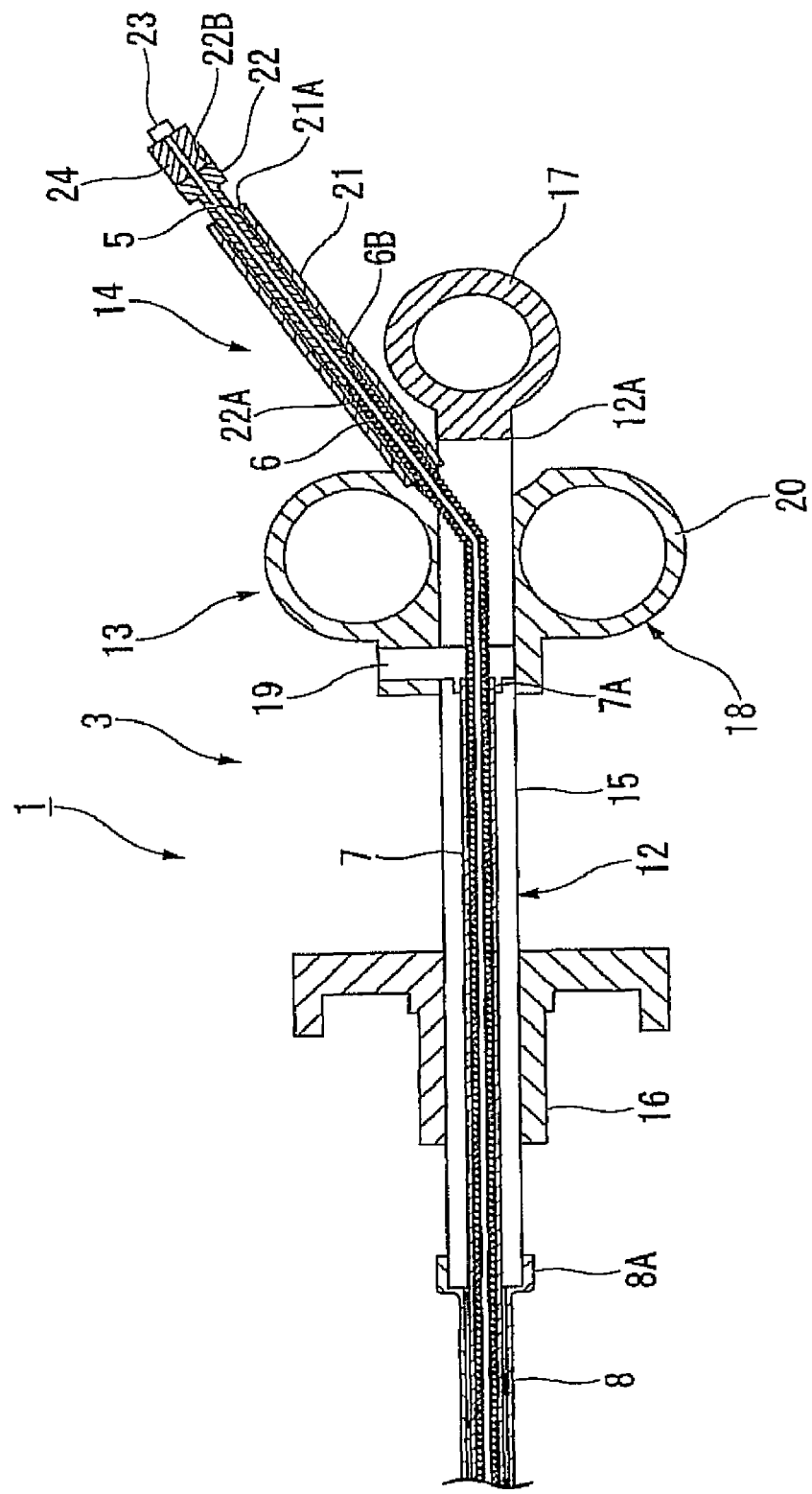
FIG. 4 is a sectional view of an operating portion of the suturing device.

FIG. 4 is a sectional view of the operating portion 3. The operating portion 3 is provided at the proximal end side of the wire 5 and the second sheath 6 and is configured to include a main body 12 fixed to the proximal end of the first sheath 8, a sliding portion 13 fitted to the main body 12 so as to be moved in the axial direction of the main body 12 in a sliding manner, and a tip operating section 14 fixed to the sliding portion 13.

The main body 12 is formed of resin or the like and is configured by arranging a pair of rod-shaped sidewall members 15 in parallel to each other. The proximal end 8A of the first sheath 8 is fixed to the distal end of the main body 12 by means of an adhesive bonding, a caulking, or the like. A substantially tubular adjuster 16 made of resin or the like is mounted in the vicinity of the distal end of the main body 12 so as to surround the pair of sidewall members 15.

The adjuster 16 can be moved in the axial direction of the main body 12 and is configured such that the adjuster 16 can be fixed at an arbitrary position with respect to the main body 12 by a fixing means such as a screw (not shown) or the like. By changing the fixing position of the adjuster 16, it becomes possible to adjust the amount of protrusion of the needle 4 from the first sheath 8, which will be described later.

The pair of sidewall members 15 is integrated with each other at the proximal end 12A of the main body 12, at which is provided an annular finger hook portion 17.

The sliding member 13 is configured to include a slider 18 fitted to the main body so as to be moved in a sliding manner, and a connection member 19 fixed to the slider 18.

The slider 18 is a substantially cylindrical member made of resin or the like and is fitted to the more proximal end 12 side of the main body 12 than the adjuster 16 so as to surround the pair of sidewall members 15. The slider 18 can be moved in the axial direction of the main body 12 between the adjuster 16 and the finger hook portion 17 in a sliding manner. A handle 20 is provided on the slider 18 so that a user can operate the slider 18 with his fingers hooked on the handle 20.

The connection member 19 is formed of resin, metal or the like, to which is fixed the proximal end 7A of the tube 7 that extends from the proximal end 8A of the first sheath 8 to the space between the pair of sidewall members 15 of the main body 12 by means of welding, adhesive bonding, or the like. That is, the proximal end 7A of the tube 7 is fixed to the slider 18 via the connection member 19, and by the sliding movement of the slider 18, the tube 7 can be moved forward and backward by a predetermined distance in the axial direction of the main body 12.

The tip operating portion 14 is configured to include a tubular member 21 fixed to the slider 18, a sheath operating member 22 that is inserted through the tubular member 21, and a wire operating knob 23 fitted to the proximal end of the wire 5.

The tubular member 21 is formed of resin or the like and is fixed on the rear side of the handle 20 of the slider 18. The wire 5 and the second sheath 6 that are extended from the proximal end 7A of the tube 7 are inserted through the tubular member 21.

The sheath operating member 22 is a tubular member made of resin or the like and is inserted into the tubular member 21 from a proximal end 21A side thereof. The sheath operating member 22 can be moved in the axial direction of the tubular member 21 in a sliding manner. The proximal end 6B of the second sheath 6 is fixed to a distal end 22A of the sheath operating member 22 by means of an adhesive bonding, a caulking, or the like. The wire 5 extended from the proximal end 6B of the second sheath 6 is passed through the inner cavity of the sheath operating member 22 and is exposed to the outside from a rear end 22B of the sheath operating member 22.

The wire operating knob 23 is a disk-shaped member and is fitted to the proximal end of the wire 5 that is exposed from the rear end 22B of the sheath operating member 22. The shape of the wire operating knob 23 is not limited to the disk shape, but may be in any shape such as the rod shape like the first anchor 106 of the suture unit 103, for example, as long as the wire operating knob 23 can be locked at the sheath operating member 22 and a wire stopper described later.

The wire stopper 24 is detachably disposed between the rear end 22B of the sheath operating member 22 and the wire operating knob 23 so as to maintain the positional relationship between the wire 5 and the second sheath 6 in a constant manner, thereby preventing malfunction of the suturing device.

As an example of the wire stopper 24, a substantially cylindrical member can be exemplified in which a portion of the outer periphery is cut out to have a substantially C-shaped section. However, the wire stopper 24 is not limited to this. The wire stopper 24 may be configured as any member such as a clip that can be fitted to the wire 5 as long as it can maintain the positional relationship between the wire 5 and the second sheath 6 in a constant manner. In the suturing device 1 of the present embodiment, the contact member 10 is configured to abut to the distal end 6A of the sheath 6 when the wire stopper 24 is interposed between the sheath operating member 22 and the wire operating knob 23.

Hereinafter, operations of the thus-constructed suturing device 1 in the operating state will be described with reference to FIGS. 1 and 5A to 11.

First, the endoscope 100 is inserted into the body of a patient or the like, and the distal end of the endoscope 100 is moved to the vicinity of a tissue as a treatment target such as a perforation or the like.

Next, as shown in FIG. 1, the distal end of the suturing device 1 is inserted into the forceps mouth 101, and the distal end portion 2 of the suturing device 1 is exposed to the outside from the endoscope channel 102.

After this, the user moves the slider 18 in the forward direction in a sliding manner, as shown in FIG. 5A. Then, as shown in FIG. 5B, the needle 4 and the suture unit 103 fitted to the needle 4 are exposed from the distal end of the first sheath 8. At this time, according to necessity, the user may adjust the fixing position of the adjuster 16 with respect to the main body 12 to allow abutment of the slider 18 to the adjuster 16, thereby adjusting the amount of protrusion of the needle 4 from the first sheath 8.

In this case, since the tip operating portion 14 is also moved in the forward direction with the forward sliding movement of the slider 18, the relative positional relationships between the tube 7 and the needle 4 and between the wire 5 and the second sheath 6 are not changed.

Figure 6:
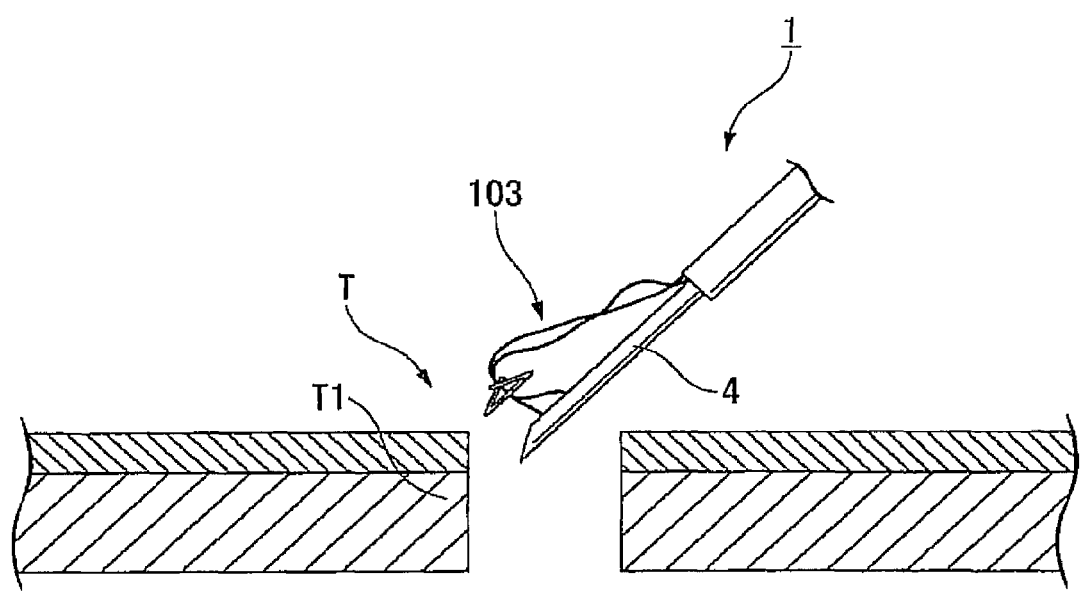
FIG. 6 is a diagram showing the state in which the suturing device is inserted into a target tissue.

Then, as shown in FIG. 6, in a state that the needle 4 is protruded out, the user moves the distal end of the suturing device 1 to the vicinity of a target tissue T around a perforation or the like and inserts the needle 4 so as to penetrate through a tissue T1.

In the state that the needle 4 is penetrated through the tissue T1, as shown in FIG. 7A, the user pushes the sheath operating member 22 of the tip operating portion 14 in the forward direction. Then, the second sheath 6 is moved in the forward direction in a sliding manner. At this time, as shown in FIG. 7B, because the distal end 6A of the second sheath 6 abuts to the contact member 10 of the wire 6, the wire 5 is pushed by the second sheath 6 and is moved in the forward direction along with the second sheath 8 while maintaining a constant relative positional relationship.

Figure 8:
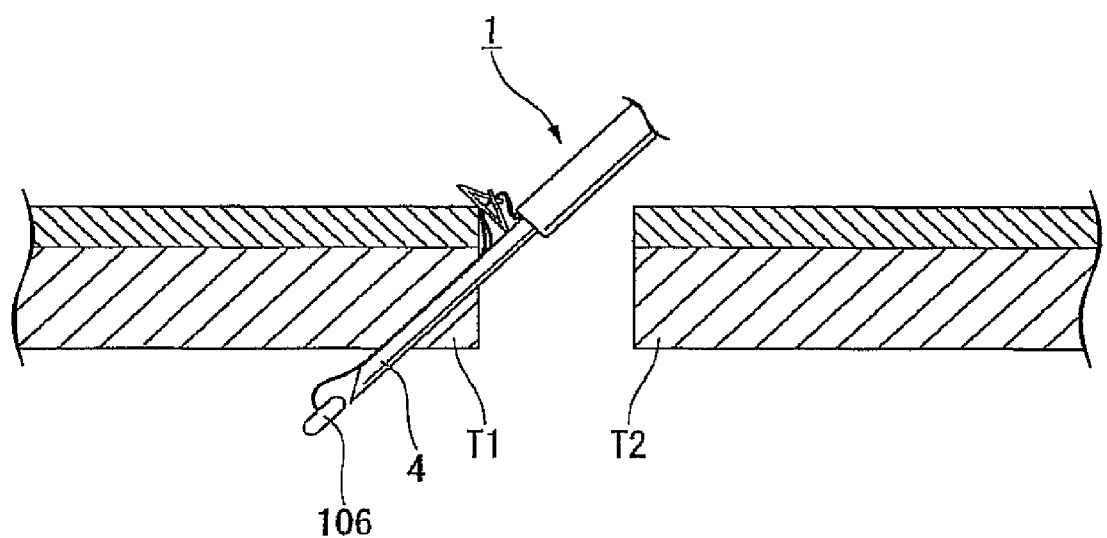
FIG. 8 is a diagram showing a step of a suturing operation by the suturing device.

The user pushes the sheath operating member 22 until the distal end 6A of the second sheath 6 abuts to a rear end 11B of the connecting tube 11 so that the forward movement of the second sheath 6 is restricted. Then, as shown in FIGS. 7B and 8, the first and second anchors 106 and 107 are moved in the forward direction by being pushed by the pressing member 9 disposed at the distal end of the wire 5, thereby allowing the first anchor 106 of the suture unit 103 to be released out from the needle 4. Then, the user can perceive the release of the first anchor 106 by sensing the feeling of abutment of the second sheath 6 to the connection tube 11.

Then, the user pulls out the needle 4 from the tissue T1. At this time, the first anchor 106 remains locked at the tissue T1. After this, the needle 4 is inserted into a tissue T2 opposite the tissue T1 with the perforation or the like disposed therebetween so as to penetrate through the tissue T2.

Figure 10:
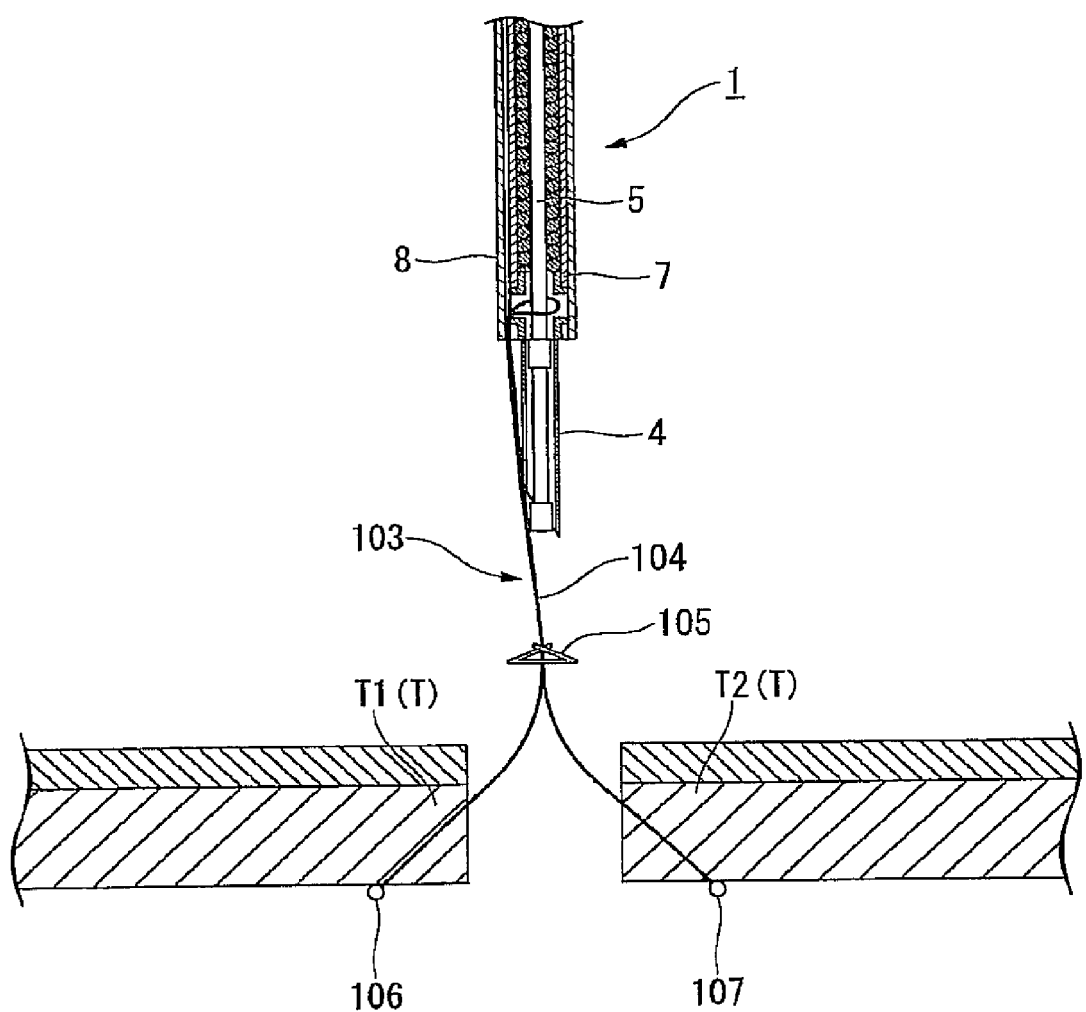
FIG. 10 is a diagram showing a step of a suturing operation by the suturing device.

After penetrating the needle 4 through the tissue T2, as shown in FIG. 9A, the user separates the wire stopper 24 from the device and operates the wire operating knob 23 to push the wire 5 in the forward direction. Then, as shown in FIG. 9B, the wire 7 is further extended to allow the second anchor 107 to be released out from the needle 4. After the second anchor 107 is released, as shown in FIG. 10, the user pulls out the needle 4 from the tissue T2, while leaving the second anchor 107 locked at the tissue T2.

In this state, the user draws the slider 18 toward the proximal end 12B side of the main body 12 so that the tube 7 and the needle 4 are received in the first sheath 8. At this time, because the tip operating portion 14 is also retracted along with the slider 18, the wire 5 is also retracted.

Then, the suture thread 104 of the suture unit 103 that is tied to the wire 5 is also received in the first sheath 8, and the stopper 105 abuts to the distal end of the first sheath 8. When the user retracts the slider 18 again, only the suture thread 104 is received in the second sheath 6 in a state that the stopper 105 is abutted to the second sheath 6. As a result, the distance between the stopper and each of the anchors 106 and 107 decreases.

Figure 11:
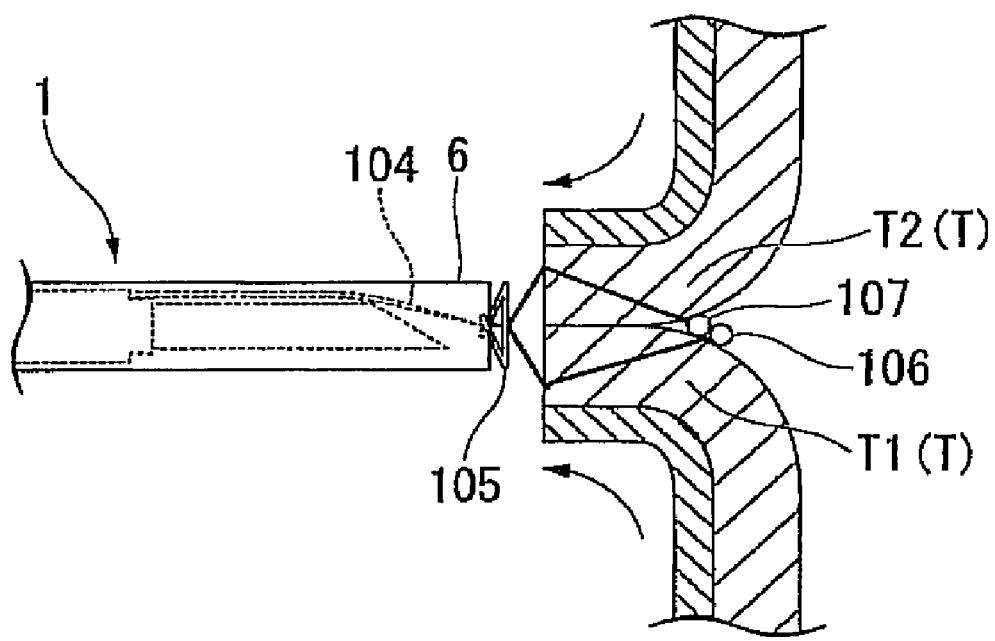
FIG. 11 is a diagram showing a step of a suturing operation by the suturing device.

Since the anchors 106 and 107 are locked at the tissues T1 and T2, respectively, as shown in FIG. 11, as the stopper 105 approaches the anchors 106 and 107, the tissues T1 and T2 are pulled toward the suturing device 1 along with the anchors 106 and 107 and are brought into close contact with each other. In this way, a suturing operation is performed on the target tissue T.

In this case, when the suture thread 104 is moved toward the mid-point portion 104B so as to be received in the first sheath 8, the engagement between the end portions 105A and 105B of the stopper 105 becomes loose. However, if the user tries to move the suture thread 104 toward the anchors 106 and 107, the movement in that direction is not allowed because the end portions 105A and 105B are more tightly engaged by the force applied by the user to the suture thread 104. That is, because the stopper 105 is only allowed to move toward the anchors 106 and 107 and movement in an opposite direction is not allowed, the suture state of the target tissue T is not loosened or released.

When the suturing operation is completed, the user pulls the wire operating knob 23 to retract the wire 5 with respect to the tube 7. When the distal end of the wire 5 is moved so as to be located on the rear side of the connection tube 1, the suture thread 104 comes off from the wire 5 and the suture unit 103 is separated from the suturing device 1. In this way, a series of treatment is completed.

According to the suturing device 1 of the present embodiment, by allowing abutment of the contact member 10 of the wire 5 to the second sheath 6, it is possible to move the wire 5 and the second sheath 6 toward the needle 4 in a sliding manner while maintaining a constant length of the protrusion of the wire 5 from the second sheath 6. In addition, by allowing abutment of the connection tube 11 to the second sheath 6, the first anchor 106 is released out from the needle 4.

Since the shapes of the connection tube 11 and the needle 4 do not change much even when the tube 7 is expanded in the axial direction at the time of releasing the anchor, a constant length of the wire 5 inserted into the needle 4 can be always maintained by abutment between the connection tube 11 and the second sheath 6. Accordingly, by allowing abutment of the connection tube 11 to the second sheath 6, it becomes possible to securely release only the first anchor 106 and to thus prevent malfunctioning such as the case in which the first and second anchors 106 and 107 are erroneously released at the same time.

Since the suture thread 104 of the suture unit 103 is inserted through the through-hole 11A of the connection tube 11 so as to be tied to the wire 5, it is possible to suture the target tissue by operating the slider 18 to cause the needle 4 to be received in the first sheath 8. Accordingly, it is possible to complete the suturing treatment only with the suturing device 1 without needing to use other mechanisms such as a clip or the like.

Since the wire stopper 24 is interposed between the sheath operating member 22 and the wire operating knob 23, it is possible to prevent malfunctioning such as the case in which when releasing the first anchor 106 by moving the second sheath 6 in the forward direction in a sliding manner, only the wire 5 is erroneously extended so that the anchors 106 and 107 are released at the same time.

In addition, since the wire operating knob 23 is configured in a shape that can be locked at the sheath operating member 22, it is possible to prevent the case in which when releasing the second anchor 107, the wire 5 is excessively extended so that the tissue is damaged by the distal end of the wire 5.

Moreover, by setting the length of the wire 5 or the tubular member 21 such that the second anchor 107 is released when the wire operating knob 23 is abutted to the sheath operating member 22, it is possible to allow the user to easily perceive the release of the second anchor 107.

In the first embodiment, description has been made for the case in which a constant relative positional relationship between the wire 5 and the second sheath 6 is maintained by the contact member 10 provided on the wire 5. However, a constant relative positional relationship may be maintained by other methods.

For example, in a state in which the wire stopper 24 is interposed between the sheath operating member 22 and the wire operating knob 23, the wire operating knob 23 and the sheath operating member 22 may be integrally gripped and moved in the forward direction in a sliding manner to push the second sheath 6 until it abuts to the connection tube 11, thereby releasing only the first anchor 106 in a secure manner. In this case, the wire stopper 24 functions as a relative position holding member that holds the relative positional relationship between the wire 5 and the second sheath 6 in a constant manner.

In the first embodiment, description has been made for the case in which the parallel member is configured as the second sheath 6 through which the wire 5 is inserted. Instead of this, the parallel member may be configured as a second wire which runs in parallel to the wire 5 and is inserted through the tube 7, in which a semi-circular or doughnut-shaped member is fixed to the distal end of the second wire. And, the suturing device may be configured such that by allowing abutment of the distal end of the second wire to the contact member 10, the wire 5 and the second wire are moved in the forward direction in a sliding manner while maintaining the relative positional relationship between the wire 5 and the second wire in a constant manner.

In the first embodiment, description has been made for the case in which the communication portion through which the suture thread 104 of the suture unit 103 is inserted is configured as the through-hole 11A that is formed in the connection tube 11. Instead of this, the communication portion may be provided on the outer peripheral surface of the tube 7 or the needle 4. In addition, the communication portion is not an essential element of the suturing device of the present invention. In a manner similar to the case of the suturing device disclosed in WO 2007-37326, the suturing operation may be performed by other mechanisms such as a clip or the like when the suture unit is separated from the suturing device after the anchor is released.

In addition, the pressing member 9 is not an essential element of the suturing device of the present invention. It may be configured such that the anchor is released by being directly pressed by the distal end of the wire 5. Similarly, the adjuster 16 is not an essential element and may not be provided.

Hereinafter, a second embodiment of the present invention will be described with reference to FIGS. 12 to 16B. A suturing device 31 of the second embodiment differs from the suturing device 1 of the first embodiment in that the second sheath is not provided in the second embodiment and that the structures of the wire and the tip operating portion of the second embodiment are different from those of the first embodiment.

The components that are identical or similar to those used in the first embodiment will be denoted by the same reference numeral and repetitious explanations thereof will be omitted.

Figure 12:
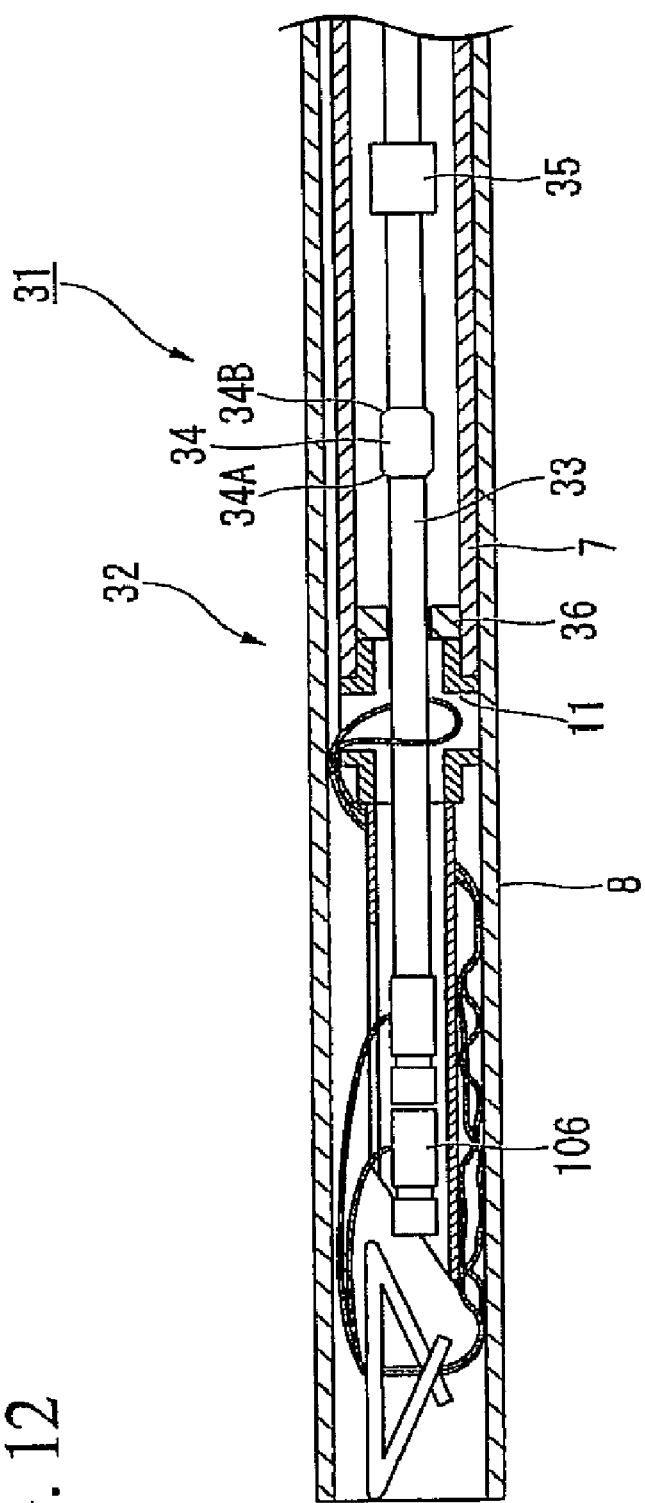
FIG. 12 is an enlarged sectional view of a distal end portion of a suturing device in accordance with a second embodiment of the present invention.

FIG. 12 is an enlarged sectional diagram of a distal end portion 32 of the suturing device 31. The suturing device 31 is not provided with the second sheath, and only a wire 33 is inserted through the tube 7.

The wire 33 is provided with a first stopper 34 for temporarily stopping a forward sliding movement of the wire 33 at a position in which the first anchor 106 is released out from the needle 4. End portions 34A and 34B in the axial direction of the first stopper 34 are tapered so that the sizes in the radial direction of the end portions 34A and 34B gradually decrease as they go toward the respective ends.

A second stopper 35 is provided at a more proximal end side of the wire 33 than the first stopper 34. The size in the radial direction of the second stopper 35 is greater than that of the first stopper 34.

An annular forward movement restricting member 36 made of an elastic material such as resin or the like is fitted to the proximal end side of the connection tube 11. The forward movement restricting member 36 is integrated with the connection tube 11 by means of an adhesive bonding or an engagement by a thread groove and is fixed to the tube 7 by means of welding or press fitting. The forward movement restricting member 36 may be integrally molded with the connection tube 11.

The inner diameter of the forward movement restricting member 36 is set smaller than the outer diameter of the first stopper 34 or the second stopper 35 so that the first and second stoppers 34 and 35 are not allowed to freely pass through the forward movement restricting member 36. However, the forward movement restricting member 36 can be elastically deformed within a predetermined range. Therefore, the sizes of the first stopper 34 and the forward movement restricting member 36 are set such that when a force stronger than a predetermined value is applied to the first stopper 34 being abutted to the forward movement restricting member 36, the forward movement restricting member 36 is deformed to allow the first stopper 34 to be passed through the forward movement restricting member 36.

Figure 13:
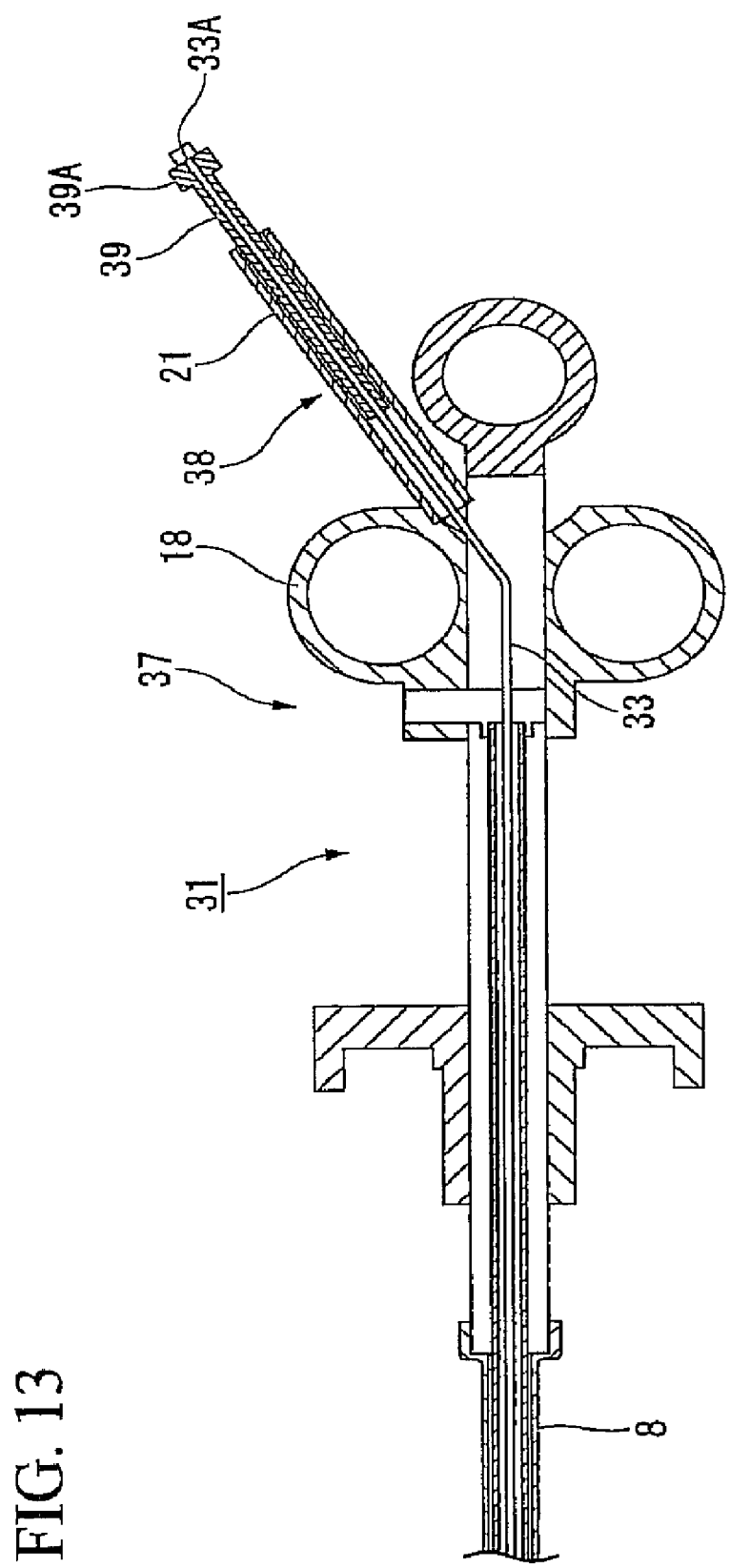
FIG. 13 is a sectional view of an operating portion of the suturing device.

FIG. 13 is a sectional view of an operating portion 37 of the suturing device 31. A proximal end 33A of the wire 33 is inserted through the tubular member 21 of a tip operating portion 38. The proximal end 33A is fixed to a wire operating member 39 that is inserted into the tubular member 21 so as to be moved in the axial direction in a sliding manner.

A flange 39A is provided at the proximal end side of the wire operating member 39. The outer diameter of the flange 39 can be expanded to a size substantially the same as that of the tubular member 21. The outer diameter of the flange 39A is not necessarily substantially the same as that of the tubular member 21 but only needs to abut to the rear end of the tubular member 21 to securely prevent the wire operating member 39 from entering into the annular member 21.

Next, operations of the thus-constructed suturing device 31 in the operating state will be described with reference to FIGS. 14A to 16B.

Figure 14A:
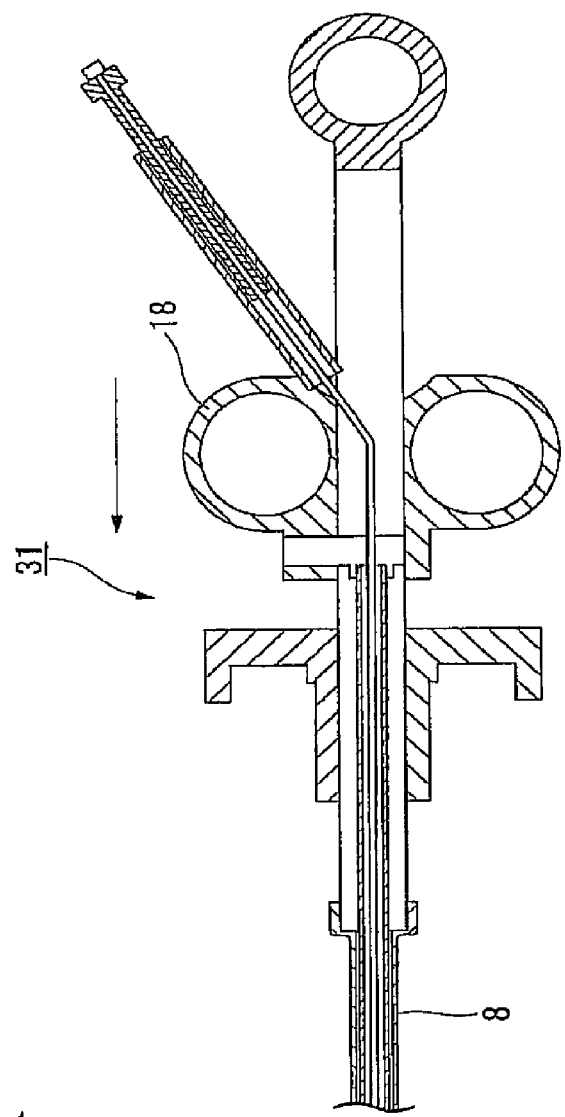
FIG. 14A is an enlarged sectional view of an operating portion of the suturing device in the operating state.
Figure 14B:
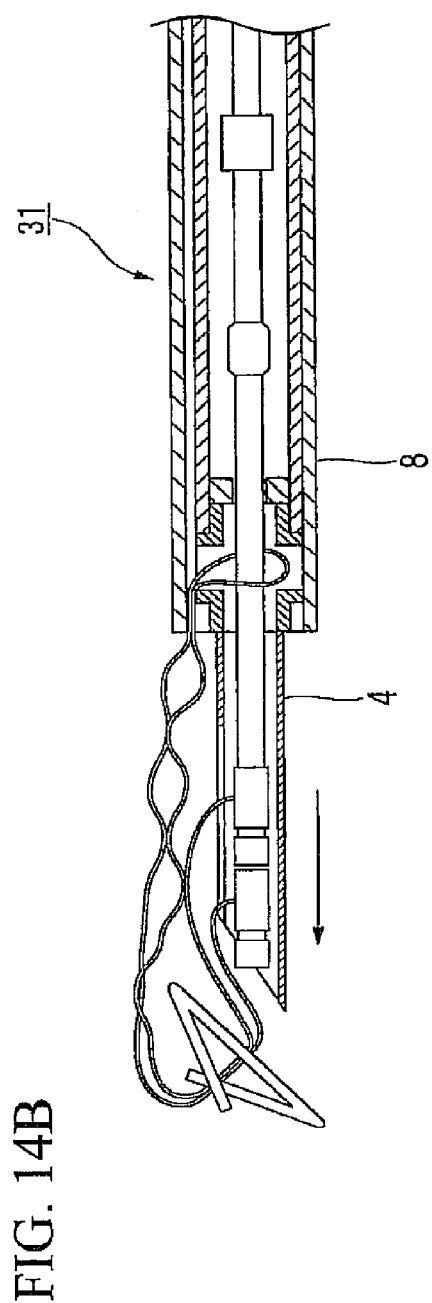
FIG. 14B is an enlarged sectional view of the distal end portion of the suturing device in the operating state.

First, as shown in FIG. 14A, the user moves the slider 18 in the forward direction in a sliding manner so as to cause the needle 4 to be protruded out from the first sheath 8, as shown in FIG. 14B. After this, in a manner similar to the case of the first embodiment, the needle 4 is inserted into a treatment target tissue so as to penetrate through the tissue.

Figure 15A:
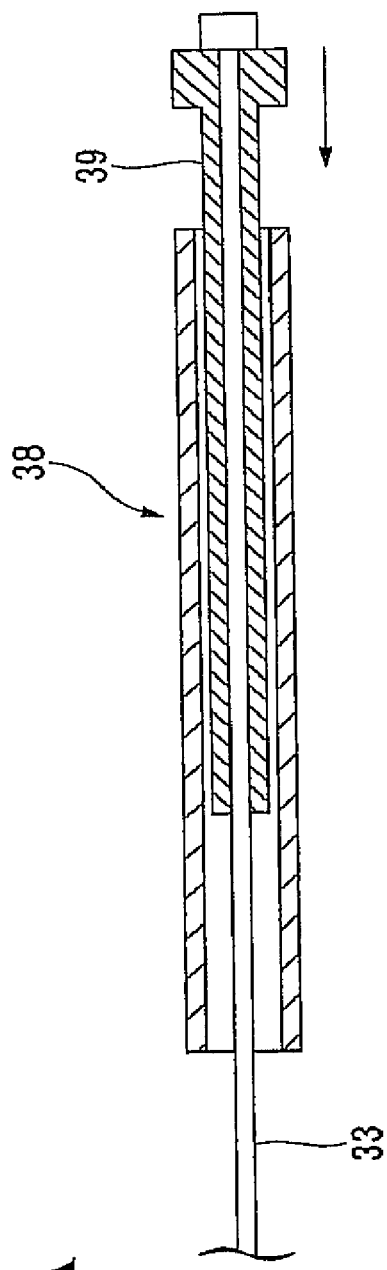
FIG. 15A is an enlarged sectional view of a tip operating portion of the suturing device in the operating state.
Figure 15B:
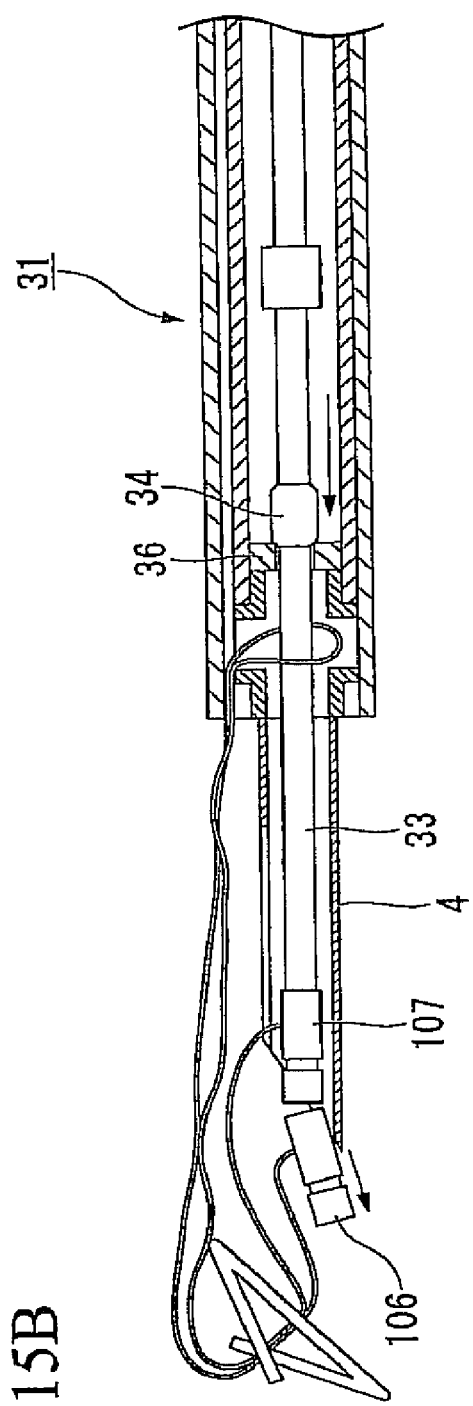
FIG. 15B is an enlarged sectional view of the distal end portion of the suturing device in the operating state.

After the needle 4 is penetrated through the tissue, as shown in FIG. 15A, the user pushes the wire operating member 39 of the tip operating portion 38 in the forward direction. Then, as shown in FIG. 15B, the wire 33 is extended to cause the forward movement restricting member 36 to abut to the first stopper 34, and the first and second anchors 106 and 107 are pushed by the distal end of the wire 33 to cause only the first anchor 106 to be released out from the needle 4. Then, the user can perceive the release of the first anchor 106 by sensing the feeling of abutment of the forward movement restricting member 36 to the first stopper 34.

After inserting the needle 4 into the other tissue, the user pushes the wire operating member 39 in the forward direction with a force greater than a predetermined value to elastically deform the forward movement restricting member 36 so that the first stopper 34 is moved toward the needle 4 by being passed through the forward movement restricting member 36.

Figure 16A:
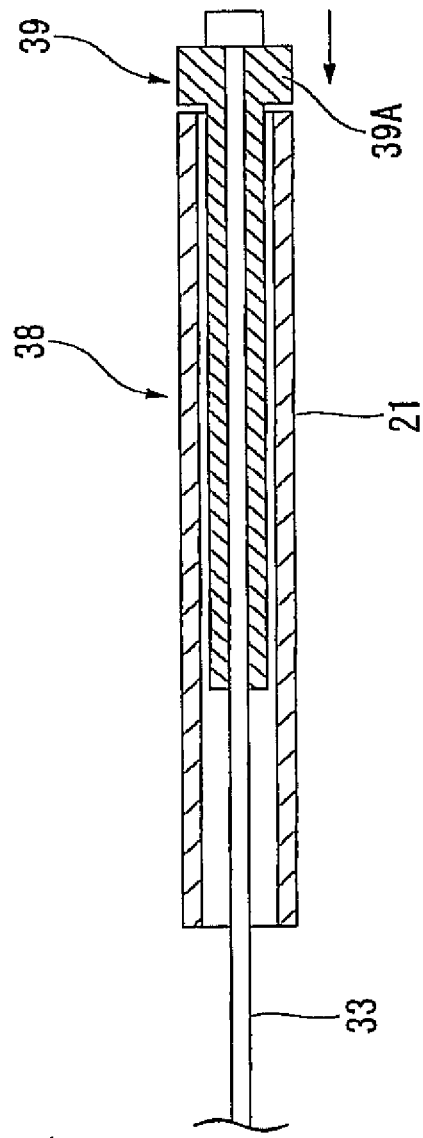
FIG. 16A is an enlarged sectional view of a tip operating portion of the suturing device in the operating state.
Figure 16B:
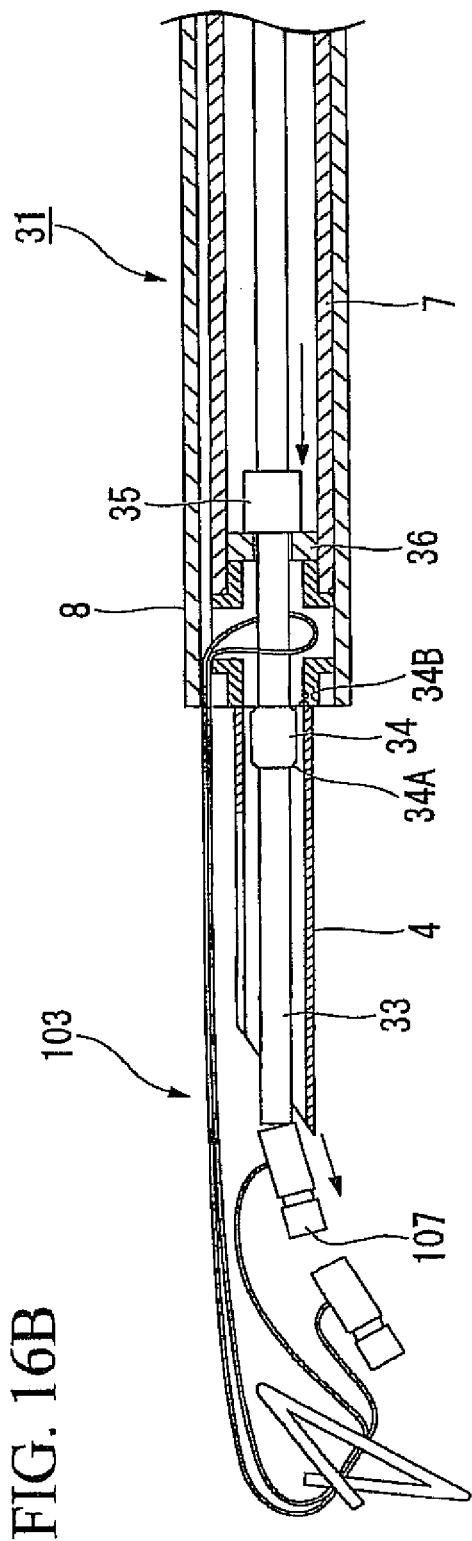
FIG. 16B is an enlarged sectional view of the distal end portion of the suturing device in the operating state.

As shown in FIG. 16A, when the user pushes again the wire operating member 39 in the forward direction, the wire 33 is further extended to cause the second stopper 35 to abut to the forward movement restricting member 36 as shown in FIG. 16B, whereby the second anchor 107 is released out from the needle 4. Then, the user can perceive the release of the second anchor 107 by sensing the feeling of abutment of the forward movement restricting member 36 to the second stopper 35. Incidentally, since the size in the radial direction of the second stopper 35 is set greater than that of the first stopper 34, the second stopper 35 is not allowed to be passed through the forward movement restricting member 36 in the elastically deformed state. As a result, it is possible to prevent the wire 33 from being excessively protruded out from the needle 4 and to thus prevent damages to the tissue or the like.

After the second anchor 107 is released, in a manner similar to the case of the first embodiment, the tube 7 and the needle 4 are retracted so as to be received in the first sheath 8, thereby suturing the target tissue. After this, by pulling the wire operating member 39 with a force greater than a predetermined value, the first stopper 34 is moved so as to be located on the rear side of the forward movement restricting member 36, thereby retracting the wire 33 to separate the suture unit 103 from the suturing device 31. In this way, a series of treatment is completed.

According to the suturing device 31 of the second embodiment, by allowing the first stopper 34 provided on the wire 33 to abut to the forward movement restricting member 36, it is possible to project only the first anchor 106 from the needle 4 in a secure manner. In addition, the user can perceive the release of the first anchor 106 by sensing the feeling of abutment of the forward movement restricting member 36 to the first stopper 34.

At this time, since the positional relationship between the forward movement restricting member 36 and the needle 4 is maintained constant even when the tube 7 is expanded, the length of the wire 33 inserted into the needle 4 when the forward movement restricting member 36 abuts to the first stopper 34 is not influenced by the expansion of the tube 7 like in the case of the first embodiment.

In addition, since the end portions 34A and 34B in the axial direction of the first stopper 34 are tapered, the first stopper 34 can be passed through the forward movement restricting member 36 in a smooth manner when the first stopper 34 receives a force greater than a predetermined value to elastically deform the forward movement restricting member 36.

In the second embodiment, description has been made for the case in which the second stopper 35 provided on the wire 33 prevents the wire 33 from being excessively protruded out from the needle 4. Instead of this, it may be configured such that the excessive protruding may be prevented by the flange 39A of the wire operating member 39. In this case, by setting the length of the wire 33 or the like such that the second anchor 107 is released by being pushed by the wire 33 when the flange 39A abuts to the tubular member 21 of the tip operating portion 38, it is possible to allow the user to easily perceive the timing at which the second anchor 107 is released by sensing the feeling of abutment of the flange 39A to the tubular member 21 while suppressing the excessive protruding of the wire 33.

Hereinabove, although preferred embodiments of the present invention have been described and illustrated, the present invention is not limited to these embodiments. Additions, omissions, substitutions, and other modifications can be made to the configurations described and illustrated above without departing from the scope and spirit of the present invention.

For example, in the embodiments described above, the description has been made for the case in which after the needle is penetrated through the tissue, the anchor is released and locked at the tissue. Instead of this, the distal end of the needle may be stopped inside the tissue and the anchor is released inside the tissue to be locked at adjacent tissues.

In addition, in the embodiments described above, the description has been made for the case in which the slider of the sliding portion is fixed to the tip operating portion through which the proximal end of the wire (and the parallel member) is inserted. However, the tip operating portion is not an essential element of the suturing device of the present invention and the proximal end of the wire or the like may be exposed to the outside. However, by inserting the wire or the like through the tip operating portion, it becomes possible to move the tube forward and backward while maintaining the relative positional relationship between the tube and the wire or the like and to thus improve operability greatly.

Accordingly, it should be noted that the scope of the present invention is to be defined by the claims appended hereto rather than being limited to the descriptions presented above.

What is claimed is:

1. A suturing device that sutures a tissue using a suture unit having a suture thread with both ends fitted to a first anchor and a second anchor, respectively, the suturing device comprising:
- a suture unit having a suture thread with both ends fitted to a first anchor and a second anchor;
- a hollow tip member receiving the first and second anchors;
- a wire having a front end inserted through the hollow tip member so that the first and second anchors can be released out from the hollow tip member;
- a flexible tube having a distal end integrally connected at a proximal end of the hollow tip member, through which the wire is inserted so as to freely move forward and backward in the axial direction of the flexible tube;
- a parallel member inserted through the flexible tube so as to freely move forward and backward in the axial direction of the flexible tube along with the wire;
- a relative position holding member fitted to the wire so as to hold constant a relative positional relationship between the wire and the parallel member, wherein the relative position holding member has an outer diameter that is larger than an outer diameter of the wire;
- a forward movement restricting member provided on the distal end of the flexible tube or the proximal end of the hollow tip member so as to restrict a forward movement of the parallel member; and
- an operating portion provided at a proximal end of the wire and the parallel member so as to operate the wire and the parallel member,
- wherein in a state in which the relative positional relationship between the wire and the parallel member is held constant by the relative position holding member, when the wire is moved in the forward direction until the forward movement of the parallel member is restricted by the forward movement restricting member, only the first anchor is released from the hollow tip member by the movement of the wire, and wherein at least one of the hollow tip member, the forward movement restricting member, and the flexible tube has a communication portion on an outer peripheral surface thereof so as to communicate with an internal cavity, and a middle portion of the suture unit is inserted into the communication portion and is tied to the wire.

2. The suturing device according to claim 1, wherein the relative position holding member is an annular contact member provided on the wire so as to abut to the parallel member.

3. The suturing device according to claim 1, the operating portion comprising:
   a main body fixed to a proximal end of a sheath through which is inserted the flexible tube;
   a sliding portion fixed to the proximal end of the flexible tube and fitted to the main body so as to be moved in the axial direction of the main body in a sliding manner; and
   a tip operating portion fixed to the sliding portion and through which are inserted the proximal ends of the wire and the parallel member.

4. The suturing device according to claim 1, wherein the parallel member is a second sheath through which is inserted the proximal end of the wire.

5. The suturing device according to claim 1, the operating portion comprises a tip operating portion, wherein a wire stopper that is detachably fitted between a rear end of the tip operating portion and the proximal end of the wire to maintain the positional relationship between the wire and the parallel member in a constant manner.

* * * * *